United States Patent [19]

Meguro et al.

[11] Patent Number: 5,061,633

[45] Date of Patent: Oct. 29, 1991

[54] METHOD FOR ANALYZING LIPID PEROXIDES USING AROMATIC PHOSPHINES

[75] Inventors: Hiroshi Meguro; Hiroshi Ohrui; Kazuaki Akasaka, all of Sendai, Japan

[73] Assignee: Tosoh Corporation, Japan

[21] Appl. No.: 489,529

[22] Filed: Mar. 7, 1990

Related U.S. Application Data

[62] Division of Ser. No. 163,544, Mar. 3, 1988, Pat. No. 4,947,000.

[30] Foreign Application Priority Data

Apr. 22, 1987 [JP] Japan ................................. 62-97577

[51] Int. Cl.⁵ ..................... G01N 21/64; G01N 33/92
[52] U.S. Cl. ..................... 436/71; 436/104; 436/135; 436/172
[58] Field of Search ................. 436/71, 103, 104, 135, 436/172

[56] References Cited

U.S. PATENT DOCUMENTS 4,036,889  7/1977  Chapdekar .
4,851,353  7/1989  Miike et al. .......................... 436/71
4,900,680  2/1990  Miyazawa et al. ................... 436/71

OTHER PUBLICATIONS

Akasaka et al., Analytical Letters, vol. 20, No. 5, pp. 731–745, 1987.
Chemical Abstract, CA:107(21)198506p.
Chemical Abstract, CA:107(13)112039d.
Analytical Abstracts, AA:50:03-F-00064.

*Primary Examiner*—Robert J. Hill, Jr.
*Attorney, Agent, or Firm*—Cushman, Darby & Cushman

[57] ABSTRACT

A method for analyzing a lipid peroxide, which comprises reacting a lipid peroxide with an aromatic phosphine compound of the formula:

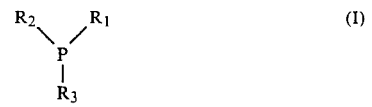

(I)

wherein each of $R_1$ to $R_3$ is an aromatic group, in a solvent, to form an aromatic phosphine oxide and observe any fluorescence of the aromatic phosphine oxide.

1 Claim, 2 Drawing Sheets

METHOD FOR ANALYZING LIPID PEROXIDES USING AROMATIC PHOSPHINES

This is a division of Application Ser. No. 07/163,544, filed Mar. 3, 1988 now U.S. Pat. No. 4,949,000.

BACKGROUND OF THE INVENTION

1. Field of the Invention

The present invention relates to a novel compound and a method for analyzing a lipid peroxide by using such a compound as a fluorescent reagent.

2. Discussion of Background

Unsaturated fatty acids or their esters are likely to be readily oxidized to form peroxides. From the standpoint of food chemistry, such oxidation is likely to lead to degradation of food products, and peroxides are known to be poisonous components. On the other hand, in the medical field, it is essential to accurately analyze lipid peroxdies for the diagnosis of aging or arteriosclerosis, and various analytical methods have been developed.

It is relatively easy to detect malondialdehyde (MDA) one of the decomposition products of lipid peroxides by a method represented by the thiobarbituric acid (TBA) color development method. However, the TBA method has various drawbacks such that the amount of MDA to be formed varies depending upon the type of the lipid peroxides, and the proportion of detectable lipid peroxides is as low as about 20%, whereby the absolute amount of the lipid peroxides can not be determined by the TBA method.

As a method having high selectivity, it is known to use an enzyme such as cyclooxygenase or glutathioneperoxidase. However, such a method has a drawback such that a special enzyme is used or it is susceptible to the influenece of an interfering substance.

Thus, it has been desired to develop a simple method having high selectivity, whereby the absolute amount of a lipid peroxide can be measured with high sensitivity.

SUMMARY OF THE INVENTION

It is an object of the present invention to obtain such a compound on an industrial scale and to provide a method for analyzing a lipid peroxide, whereby the reaction with the lipid peroxide can be conducted simply under a mild condition and the analysis can be conducted with high sensitivity.

Namely, the present invention provides an aromatic phosphine compound of the formula:

wherein each of $R_1$ to $R_3$ is an aromatic group, or an oxide thereof.

Further, the present invention provides a method for analyzing a lipid peroxide, which comprises reacting a lipid peroxide with an aromatic phosphine compound of the formula:

wherein each of $R_1$ to $R_3$ is an aromatic group, in a solvent.

BRIEF DESCRISPTION OF THE DRAWINGS

DETAILED DESCRIPTION OF THE PREFERRED EMBODIMENTS

Figure 1:
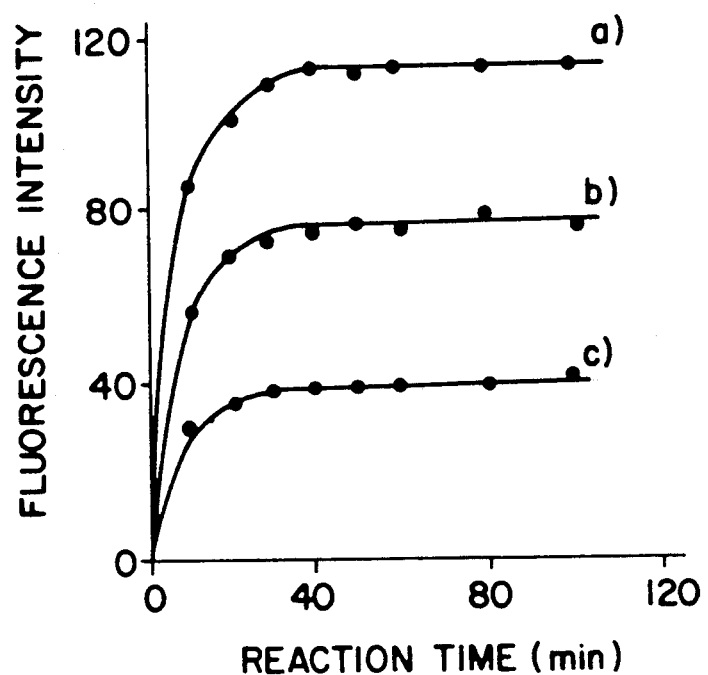
FIG. 1 is a graph showing the relation between the reaction time and the intensity of fluorescence, obtained in Example 5 of the present invention.

Now, the present invention will be described in detail.

The aromatic phosphine of the present invention can be produced by various methods. A typical method for the production will be given below.

Triphenylphosphine and lithium as a reactive base are suspended in an organic solvent, and the suspension is stirred at room temperature for a few hours. Then, an alkali metal halide dissolved in an organic solvent is added thereto, and the mixture is refluxed under heating for a short period of time. After cooling, the reaction solution is filtered through a glass column packed with e.g. glass wool to remove unreacted excess lithium. Then, in order to introduce a chromophore for fluorescence, the above-mentioned reaction solution is poured into an organic solvent containing a halogenated aromatic compound synthesized from an aromatic compound having a chromophore for fluorescence and a metal halide (D.C. Nohebel, Proc. Chem. Soc., 307 (1961). Then, the refluxing is continued under heating for a few hours.

The above operation is preferably conducted in the presence of an inert gas in order to prevent oxidation of the starting materials and the resulting phosphine. After cooling, the reaction solution is poured into water to dissolve excess salt and base, and then the organic phosphine compound is extracted with a non-polar organic solvent such as chloroform. The compound is subjected to separation and purification by column chromatography using silica gel. The solvent is evaporated under reduced pressure to dryness and the residue is dissolved again in a solvent having a slightly high polarity and recrystallized by an addition of a solvent having low polarity such as hexane.

Such a compound can readily be identified by a usual analytical method such as elemental analysis, mass spectrometry or infrared absorption spectrum.

The aromatic phosphine compound of the present invention itself is non-fluorescent, but when reacted with a lipid peroxide, it is converted to an aromatic phosphine oxide exhibiting a blue fluorescence, as represented by the following reaction formula:

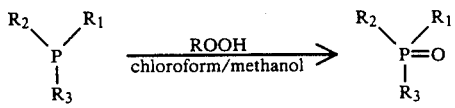

Namely, the aromatic phosphine oxide is obtainable by mixing the peroxide and the aromatic phosphine in a solvent and reacting them at 60° C. for 60 minutes.

As the lipid peroxide, there may be mentioned peroxides of fatty acids such as linolic acid and linolenic acid in a living body or in a food product.

As the solvent, a usual organic solvent such as chloroform, dichloromethane or methanol may be mentioned. From the extraction efficiency of lipid peroxides, it is preferred to use a mixture of chloroform and methanol. At the time of extraction, an antioxidant such as butylhydroxytoluene (BHT) may be added to prevent oxidation of lipids without affecting the analysis.

The reaction may proceed even when the reaction temperature is low. However, in order to complete the reaction in a short period of time, it is preferred to conduct the reaction at 60° C. Here, no substantial decomposition of the lipid peroxide takes place, and there is no substantial influence over the quantitative analysis. The reactivity of the aromatic phosphine and the lipid peroxide is affected by the degree of their respective structural steric hindrance. Namely, the larger the chromophore for fluorescence around the phosphorus atom of the aromatic phosphine compound and the more complex the structure of the lipid peroxide around the peroxide moiety, the slower the reaction becomes.

As described in the foregoing, the present invention has the following advantages:

1) An aromatic phosphine compound can readily be prepared in a short step by using triphenylphosphine as the starting material;
2) The aromatic phosphine compound is non-fluorescent, but when reacted with a lipid peroxide, it emits a fluorescence with a strong blue color;
3) The reaction of the aromatic phosphine compound and the lipid peroxide can be conducted under a relatively mild condition i.e. at 60° C. for 60 minutes;
4) No catalyst is required for the reaction of the lipid peroxide and the aromatic phosphine;
5) The aromatic phosphine compound is stable against oxidation in air, and it is converted to an oxide solely by the oxidation with the lipid peroxide;
6) The reaction of the aromatic phosphine compound and the lipid peroxide proceeds quantitatively, whereby the absolute amount of the lipid peroxide can be determined with high sensitivity; and
7) The method can be applied not only to the extraction of food products but also to the analysis of lipid peroxides in blood or in a living organ. Now, the present invention will be described in further detail with reference to Examples. However, it should be understood that the present invention is by no means restricted by these specific Examples.

EXAMPLE 1

Into a tetrahydrofuran (THF) solvent, 5.09 g (19.4 mM) of triphenylphosphine as starting material and 410 mg (59.1 mm) of lithium were suspended, and the suspension was stirred under a nitrogen stream at room temperature for 3 hours. Then, 20 ml of a THF solution of tert-butyl chloride (0.97M) was added thereto, and the mixture was refluxed under heating for 10 minutes. After cooling, the reaction solution was filtered through a glass column packed with glass wool under a nitrogen stream to remove excess lithium in the reaction solution. Then, a reaction solution filtered in a similar manner under a nitrogen stream was transferred to a three necked flask having a capacity of 500 ml and containing 5.0 g (28 mM) of 1-bromoanthracene, and the mixture was refluxed under heating for 3.5 hours.

Then, the reaction solution was poured into water, and 9-anthryldiphenylphosphine (ADPP) was extracted with 150 ml of chloroform. As a purification means of ADPP, the separation of ADPP from unreacted material and reaction by-products was conducted firstly by silica gel chromatography (hexane/benzene=8/2). Then, the solvent was evaporated under reduced pressure to dryness, and the residue was recrystallized from ethyl acetate solvent to obtain 627 ml of ADPP as yellow crystals. (Yield: 8.9%, mp: 203.5° C.)

ADPP was confirmed by the elemental analysis, infrared absorption and mass spectrometry. The results thereby obtained are shown below.

| Elemental analysis | C % | H % |
| --- | --- | --- |
| Calculated values: | 86.16 | 5.28 |
| Measured values: | 86.00 | 5.57 |

$IR_{KBr}cm^{-1}$: 1590, 1470 (Arom); 1425, 1010, 990 (P-Carom).

FD Mass (M+1): 363.

EXAMPLE 2

To 66 mg (18.2 mM) of ADPP dissolved in a mixture of chloroform/methanol (1/1), a few drops of a about 30% hydrogen peroxide aqueous solution was added. The reaction solution was subjected to silica gel column chromatography (chloroform) to obtain crude ADPP oxide obtained by separating it from unreacted substance, and the oxide was recrystallied from chloroform to obtain 35 mg of yellowish white crystals. (Yield: 51.6%; mp: 184°–185° C.).

The ADPP oxide was confirmed by the elemental analysis, infrared absorption and mass spectrometry. The results thereby obtained are shown below.

| Elemental analysis | C % | H % |
| --- | --- | --- |
| Calculated values: | 82.52 | 5.06 |
| Measured values: | 82.12 | 5.07 |

$IR_{KBr}cm^{-1}$: 1610, 1500 (Arom); 1430, 1010, 990 (P-Carom).

FD Mass (M+1): 379.

EXAMPLE 3

In the same manner as in Example 1, diphenyl-1-pyrenylphosphine (DPPP) was prepared by using 1-bromopyrene as the organic compound having a chromophore for fluorescence. Likewise, 1-naphthylenediphenylphosphine (NDPP) was prepared by using 1-bromonaphthalene. DPPP and NDPP were confirmed by the elemental analyses, infrared absorption and mass spectrometry. The results thereby obtained are shown below.

DPPP (mp: 171°–174° C.).

| Elemental analysis | C % | H % |
| --- | --- | --- |
| Calculated values: | 87.02 | 4.95 |
| Measured values: | 86.36 | 5.14 |

$IR_{KBr}cm^{-1}$: 1590, 1470 (Arom); 1425, 1070, 990 (P-Carom).

FD Mass (M+1): 387.

NDPP (mp: 121° C.).

| Elemental analysis | C % | H % |
| --- | --- | --- |
| Calculated values: | 84.59 | 5.48 |

| Elemental analysis | C % | H % |
| --- | --- | --- |
| Measured values: | 84.17 | 5.49 |

$IR_{KBr}cm^{-1}$: 1580, 1470 (Arom); 1430, 1020, 1000 (P-Carom).

FD Mass (M+1): 313.

EXAMPLE 4

In the same manner as in Example 2, DPPP oxide and NDPP oxide were obtained. DPPP oxide and NDPP oxide were confirmed by the elemental analyses, infrared absorption and mass spectrometry. The results thereby obtained are shown below.

DPPP oxide (mp: 245° C.).

| Elemental analysis | C % | H % |
| --- | --- | --- |
| Calculated values: | 83.56 | 4.75 |
| Measured values: | 82.50 | 4.99 |

$IR_{KBr}cm^{-1}$: 1580, 1470 (Arom); 1439, 1025, 990 (P-Carom).

FD Mass (M+1): 403.

NDPP oxide (mp: 121° C.).

| Elemental analysis | C % | H % |
| --- | --- | --- |
| Calculated values: | 84.59 | 5.48 |
| Measured values: | 84.17 | 5.49 |

$IR_{KBr}cm^{-1}$: 1580, 1470 (Arom); 1430, 1020, 1000 (P-Carom).

FD Mass (M+1): 313.

EXAMPLE 5

Linolic acid oxide was used as the lipid peroxide, and it was dissolved in a mixture of methanol/chloroform (½) containing butylhydroxytoluene (DHT) as an antioxidant so that the concentration would be 7.6 mM(a), 5.1 mM(b) and 2.5 mM(c). 100 ml of each solution was put into a test tube equipped with a stirrer and contaning 50 ml of a solution (1 mg/10 ml) of diphenylpyrenylphosphine (DPPP) dissolved in a mixture of methanol/chloroform (1/1). The test tube was sealed by a stopper and left to stand in hot bath at 60° C. To examine the production of DPPP oxide as time passed, after expiration a predetermined time, the test tube was rapidly cooled to room temperature, and 3 ml of methanol was added thereto. Then, the intensity of fluorescence at 380 nm was measured (excitation wavelength: 352 nm). The results are shown in FIG. 1. As is aparent from FIG. 1, the reaction completed in 60 minutes when the reaction temperature was 60°.

EXAMPLE 6

The interrelation between the peroxide value according to the conventional iodometry method (C. H. Loaa., Pro. Royal. Sox. London Ser. B., 108 175 (1931)) and the amount of the peroxide according to the method of the present invention was examined. The reaction of the lipid peroxide with DPPP was conducted in the same manner as in Example 5.

In the method of the present invention, the amount of the peroxide is measured as the molar concentration in 1 g of the sample. The molar concentration was converted to the peroxide value according to the conventional method.

Figure 2:
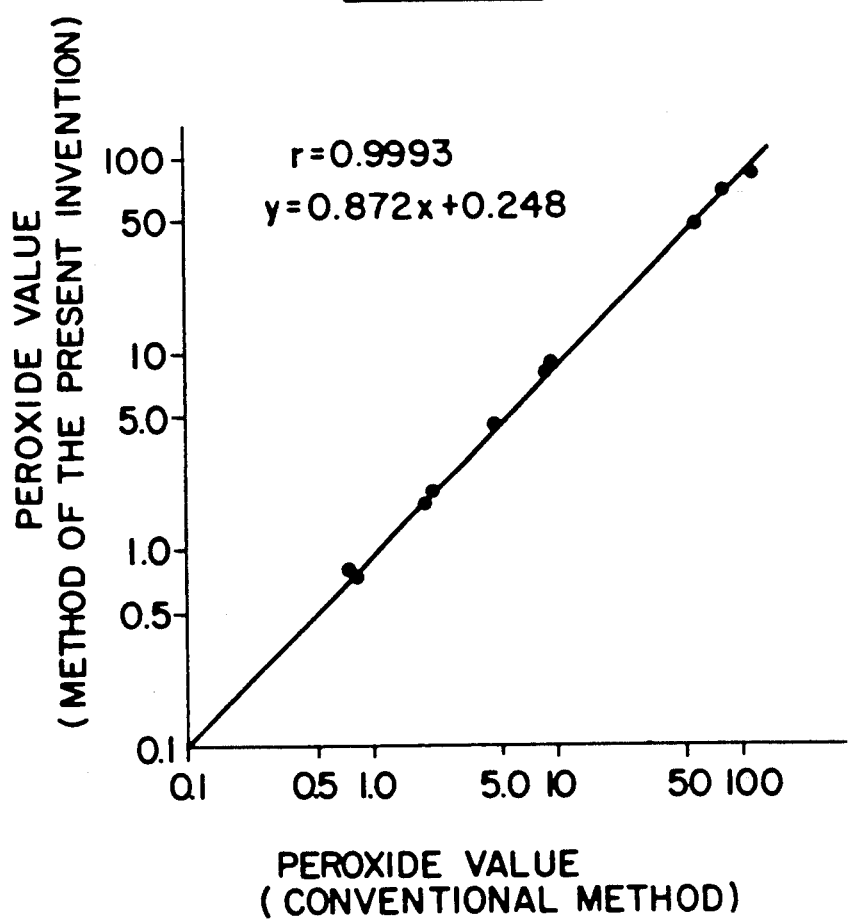
FIG. 2 is a graph showing the interrelation between the method of the present invention and a conventional method.

The results are shown in FIG. 2, which indicates an excellent interrelation with an interrelation coefficient of 0.9993 and with an interrelation equation of y (method of the present invention)=0.872×(conventional method) +0.248.

What is claimed is:

1. A method for analyzing a lipid peroxide, which comprises reacting a lipid peroxide with an aromatic phosphine compound of the formula:

wherein each of $R_1$ to $R_3$ is an aromatic group, in a solvent, to form an aromatic phosphine oxide and observe any fluorescence of the aromatic phosphine oxide.

* * * * *